(12) United States Patent
Francescatti et al.

(10) Patent No.: US 7,727,137 B2
(45) Date of Patent: Jun. 1, 2010

(54) BALLOON BRACHYTHERAPY APPLICATOR AND METHOD

(75) Inventors: Darius Francescatti, Barrington, IL (US); David J. Hoffmann, Clayton, MO (US); Scott Tremberth, Henderson, NV (US); Michael Klein, Menlo Park, CA (US); Paul A. Lovoi, Saratoga, CA (US); James E. Jervis, Atherton, CA (US)

(73) Assignee: Xoft, Inc., Sunnyvale, CA (US)

( * ) Notice: Subject to any disclaimer, the term of this patent is extended or adjusted under 35 U.S.C. 154(b) by 181 days.

(21) Appl. No.: 11/871,116

(22) Filed: Oct. 11, 2007

(65) Prior Publication Data

US 2009/0209802 A1    Aug. 20, 2009

Related U.S. Application Data

(60) Provisional application No. 60/851,687, filed on Oct. 13, 2006.

(51) Int. Cl.
*A61M 36/00* (2006.01)
*A61M 36/04* (2006.01)
*A61N 5/00* (2006.01)

(52) U.S. Cl. .................................. 600/7; 600/3; 600/1
(58) Field of Classification Search ................ 600/1–8, 600/263, 264, 288.01–288.04; *A61M 36/00, A61M 36/04; A61N 5/00*
See application file for complete search history.

(56) References Cited

U.S. PATENT DOCUMENTS

| | | | |
|---|---|---|---|
| 4,706,652 A * | 11/1987 | Horowitz | 600/7 |
| 4,871,358 A | 10/1989 | Gold | |
| 5,566,221 A | 10/1996 | Smith et al. | |
| 5,611,767 A * | 3/1997 | Williams | 600/2 |
| 5,748,699 A | 5/1998 | Smith | |
| 5,797,886 A * | 8/1998 | Roth et al. | 604/264 |
| 5,947,953 A | 9/1999 | Ash et al. | |
| 6,213,973 B1 | 4/2001 | Eliasen et al. | |
| 6,319,188 B1 | 11/2001 | Lovoi | |
| 6,364,892 B1 | 4/2002 | Jervis | |
| 6,540,764 B1 | 4/2003 | Kieturakis et al. | |
| 6,923,754 B2 * | 8/2005 | Lubock | 600/3 |
| 6,987,835 B2 | 1/2006 | Lovoi | |
| 7,179,272 B2 | 2/2007 | Kieturakis et al. | |
| 2001/0049502 A1 * | 12/2001 | Chen | 604/167.06 |

(Continued)

OTHER PUBLICATIONS

Muller, J.H., "Radiotherapy of Bladder Cancer by Means of Rubber Balloons Filled In Situ with Solutions of a Radioactive Isotope (Co60)", Cancer, Sep.-Oct. 1995, pp. 1035-1043.

(Continued)

*Primary Examiner*—Charles A Marmor, II
*Assistant Examiner*—Catherine E. Burk
(74) *Attorney, Agent, or Firm*—Thomas M. Freiburger

(57) ABSTRACT

Methods and applicator apparatus are disclosed for brachytherapy treatment of tissue surrounding a cavity in a patient, particularly a resection cavity. In treatment regimes requiring recovery time between successive radiation treatments, applicators of the invention are retained under the skin, with the skin allowed to at least partially heal, and are re-accessed later for one or more subsequent treatments. To reduce patient discomfort an anesthetic agent can be infused through the applicator to patient tissue, for insertion, balloon inflation or removal of the applicator.

16 Claims, 11 Drawing Sheets

U.S. PATENT DOCUMENTS

| | | | |
|---|---|---|---|
| 2004/0116767 A1* | 6/2004 | Lebovic et al. | 600/7 |
| 2004/0245483 A1* | 12/2004 | Smit et al. | 250/506.1 |
| 2005/0101860 A1 | 5/2005 | Patrick et al. | |
| 2006/0100475 A1 | 5/2006 | White et al. | |
| 2006/0206178 A1 | 9/2006 | Kim | |
| 2007/0270627 A1* | 11/2007 | Cutrer et al. | 600/7 |

OTHER PUBLICATIONS

Low-Beer, B.V.A., "The Clinical Use of Radioisotopes", Charles C. Thomas Publ., 1950, pp. 343-349.

Ashpole et al., R.D., "A New Technique of Brachytherapy for Malignant Gliomas with Caesium 137: A New Method Utilizing a New Afterloading System", Clinical Oncology, vol. 2, (1990), pp. 333-337.

Jobson et al., J.J., "Timing of Radiotherapy and Survival Benefit in Breast Cancer", Breast Cancer Research and Treatment, (2006) 99:289-294.

Smitt & Kirby, "Dose-Volume Characteristics of a 50-kV Electronic Brachytherapy Source" Brachytherapy, 6 (2007), 207-211.

* cited by examiner

BALLOON BRACHYTHERAPY APPLICATOR AND METHOD

This application claims benefit from provisional application No. 60/851,687, filed Oct. 13, 2006.

BACKGROUND OF THE INVENTION

The invention concerns balloon brachytherapy.

Balloon brachytherapy has been known since at least the 1950s, and involves placing a source of radiation within the body, generally near a tumor or within an excision site following removal of a tumor. The purpose or objective is to irradiate the tumor or the margins around the tumor excision cavity. The usual further objective is to provide dose levels of radiation to a target tissue volume surrounding the excision cavity which attain a therapeutic minimum, but below a level capable of producing significant normal-cell tissue necrosis. To accomplish this, a balloon applicator is employed into which the source of radiation is positioned.

Several improvements in applicator design are desirable. In anticipation of radiation therapy to follow complete or partial tumor excision, applicators can be placed within the excision cavity intraoperatively, i.e., during the surgical procedure and before the resection incision is closed. They may also be placed during a separate procedure at a later date when it has been decided to proceed with radiation therapy. Access to the excision cavity for radiation therapy may be through the original incision, or through a different incision purposely created for the applicator. A separate access site might be preferred if the anticipated dose distribution from the brachytherapy protocol, given the location of the excision cavity and proximity to sensitive tissue structures, might place those tissues at risk. When placed intraoperatively, the incision is closed around a sheath, which extends through and outside the skin of the patient. The applicator balloon is usually inflated when the incision is closed, and remains in place until radiation treatment is abandoned or the protocol completed, at which time the balloon is deflated and the applicator surgically removed.

Current or prior art balloon applicators include those described in J. H. Muller, *Radiotherapy of Bladder Cancer by Means of Rubber Balloons Filled In Situ with Solutions of a Radioactive Isotope ($Co^{60}$), Cancer*, September-October, 1955, pp 1035-1043; *The Clinical Use of Radioisotopes*, B. V. A Low-Beer, Charles C. Thomas Publ., 1950; *A New Technique of Brachytherapy for Malignant Gliomas with Caesium 137: A New Method Utilizing a New Afterloading System*, R. D. Ashpole, et al, Clinical Oncology, vol. 2, 333-337, (1990); and U.S. Pat. No. 5,566,221. Radiation sources used for brachytherapy include small x-ray tubes as disclosed in U.S. Pat. Nos. 5,566,221, 6,319,188, and 6,987,835. Solid high-dose radiation isotope sources may be used, for example those sold by Varian Medical Systems, Inc., Palo Alto, Calif., and fluid isotope sources, for example a solution or slurry of radionuclides such as I-125 or Au-198. X-ray tubes offer both patient and therapist advantages including substantially reduced amounts of radiation and control of the radiation source. Radioisotope sources must be used inside bunkers lined with lead or other absorbers, with the patient being isolated in the bunker. Use of x-ray tubes is not subject to these restrictions. Unlike an x-ray tube, radioisotopes cannot be turned on and off, but rather emit radiation continuously. Those skilled in the art will appreciate that there are additional substantial differences between x-ray tube brachytherapy and radionuclide brachytherapy.

Radiation treatment often follows days after surgery, but preferably it follows weeks after surgery [See *Breast Cancer Research and Treatment*, J. J. Jobson, et al (2006) 99:289294] and such protracted exposure of the surgical wound at the entry of the applicator sheath through the skin prior to commencing radiotherapy provides a substantial risk of infection that can compromise the resection cavity, and cause additional serious complications for the patient. Also, there can be significant discomfort if the applicator is placed intraoperatively and remains indwelling for an extended period and is perhaps inflated later prior to radiotherapy, or is placed and inflated later in a subsequent procedure, disturbing anatomy which is still sensitive from the resection. It would be beneficial to have an applicator and method which would minimize or eliminate this discomfort and infection risk, but otherwise offer the same or improved functionality and convenience as current applicators. Copending application Ser. No. 10/464,140, filed Jun. 18, 2003, discloses methods of intraoperative brachytherapy using electronic x-ray tubes, and the disclosure of that application is incorporated by reference herein. Copending application Ser. No. 11/811,069 discloses an everting gynecological discloses an everting gynecological applicator, and the disclosure of that applicator is also incorporated by reference herein.

SUMMARY OF THE INVENTION

This invention is directed to placing apparatus within a tumor resection cavity, preferably intraoperatively, such that the cavity may be easily reaccessed later for brachytherapy, but which allows the skin to be closed in the interim, thus facilitating healing. This method eliminates the need for apparatus passing through the skin between the resection procedure and initiation of radiation therapy. Such protruding apparatus can be easily bumped or disturbed, causing pain and perhaps infection, thereby impeding the healing process.

The apparatus of this invention comprises an expandable balloon which can be inflated within the excision cavity intraoperatively, after which the incision used to create or access the cavity is closed completely so healing can progress. At a later date when and if brachytherapy is to proceed, balloon access is reacquired, either by reopening the original incision or through a new incision at a preferable site. If such treatment is contra-indicated, the apparatus is used for deflation if necessary, and for removal of the apparatus entirely.

Advantageously the balloon apparatus further comprises an integral extension or a hollow sheath having length and forming a single longitudinal channel or a plurality of such channels which communicate with or extend into the balloon, and when accessed to commence radiation treatment, facilitate inflation or other functionality as outlined below. The channels can be fluid channels, such as for balloon inflation, infusion of anesthetic or therapeutic agents, cavity drainage, or they can accommodate instruments, inner sheaths or catheters, such as a catheter with a radiation source at its distal tip. When reaccessed by means of a new incision (or by reopening an old incision), the extension can be pulled outwardly to provide easy access to the balloon through the incision.

In a further embodiment, a housing at the proximal end of the sheath is affixed to the underside of the skin of the patient in a preferred location, preferably intraoperatively. The housing provides for self-sealing, percutaneous access to the sheath and balloon, but in other respects provides the same functionality as described above.

In yet another embodiment, the balloon is eliminated and a sheath provided which extends from under the skin well into the excision cavity. At commencement of radiotherapy, the skin over the closed end of the implanted sheath is incised, and the sheath withdrawn, but not so far as to lose communication with the excision cavity. The end of the sheath, if closed, is the cut off or otherwise removed, and a conventional balloon applicator (see *Brachytherapy*, 6 (2007), 207-211, Smitt & Kirby, "Dose—volume characteristics of a 50-kV electronic brachytherapy source for intracavitary accelerated partial breast irradiation) inserted into the implanted sheath such that the balloon is within the cavity, and the balloon inflated. The source catheter can then be inserted and brachytherapy begun.

In general, it is preferable that there be a portion of the sheath or balloon extension which protrudes outside of the patient's skin and which can be later further extended, gripped and/or manipulated. Such extensions can be corrugated, everted, and/or elastic such that they can be stretched outwardly beyond the surface of the patient's skin.

In the apparatus described above, it is preferable that a channel providing for drug or anesthetic delivery to, or seroma drainage from the cavity before commencing and/or during radiation therapy be incorporated in the apparatus of the invention.

From the description above, other embodiments will occur to those of skill in the art and are to be considered as within the scope of the invention.

DESCRIPTION OF THE PREFERRED EMBODIMENTS

The method of this invention comprises placing apparatus within or proximate a tumor resection cavity which facilitates easy reaccess to the cavity for brachytherapy. Such apparatus is preferably placed intraoperatively (but could be placed later in a separate procedure) and allows the skin to be closed pending a decision to proceed with, or to abandon brachytherapy. This method eliminates the need for apparatus passing through the skin for a protracted period and optionally provides for administration of therapeutic agents or anesthetic during subsequent apparatus manipulation or the brachytherapy treatment itself. The embodiments described below are used in conjunction with conventional brachytherapy apparatus.

The embodiments of the invention generally provide a convenient path for conventional brachytherapy apparatus to be inserted into the resection cavity some protracted time after the resection procedure itself. The procedure to reaccess the cavity begins with an incision (or percutaneous stick) to reach a portion of the implanted apparatus which is preferably near the skin of the patient. Next, an extension of the apparatus is established which protrudes through the skin at its proximal end, and leads into the resection cavity. Subsequent steps will depend on the invention embodiment chosen, but all lead to facilitating use of conventional brachytherapy methods and/or apparatus to complete the brachytherapy.

Figure 1:
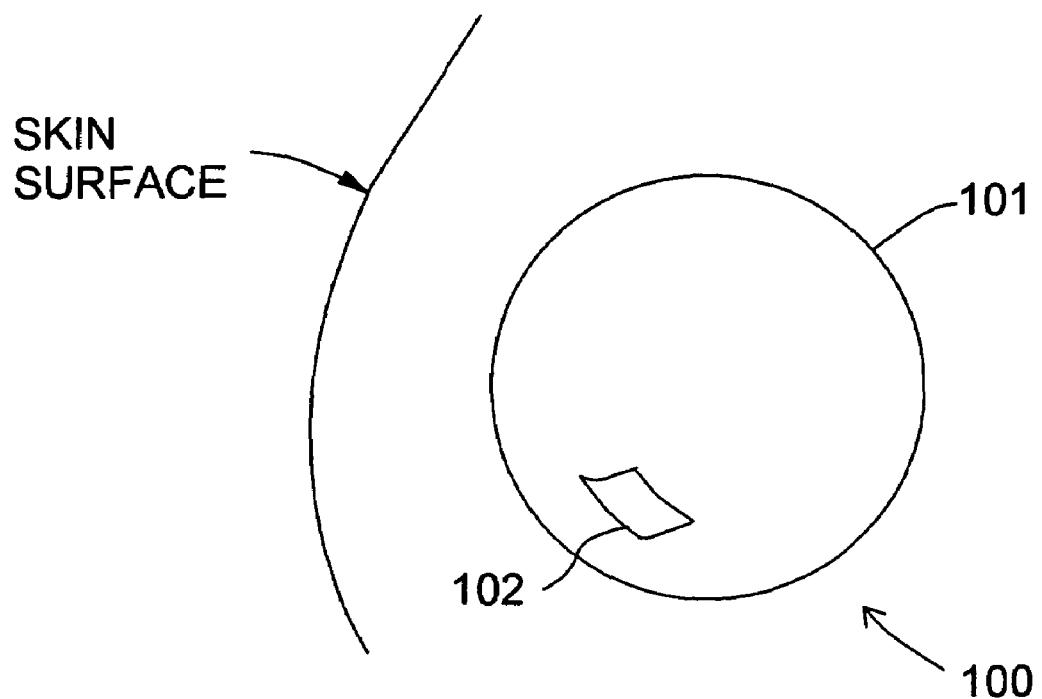
FIG. 1 is a schematic section view through tissue showing an inflated balloon placed in an excision cavity with the incision closed (incision not shown).

FIG. 1 depicts an apparatus 100 including a simple balloon 101 placed intraoperatively within the body and inflated in an excision cavity. A self-sealing patch 102 anywhere on the surface of the balloon suffices for inflation by a syringe. The patch can be relatively small compared to the balloon surface, or it can cover a significant portion of the surface. Self-sealing patch materials include various gel materials known in the art and silicone elastomers. Suitable balloon materials include polyurethanes and silicone rubbers. At one extreme, the material may be selected, and balloons may be designed, which are sufficiently elastic to conform to shape of the excision cavity. At the other extreme, materials and designs can be chosen which will substantially shape the cavity so that it conforms to a desired configuration, for example, so that it mimics the shape of the isodose surfaces which are generated by the brachytherapy source and apparatus in total and/or which correspond to the planned therapy. It is therefore also clear that balloon designs can be devised with properties between these extremes. As an example of such apparatus 100, if the excision cavity is spherical, or can be forced into a spherical shape, an isotropic point source and spherical balloon filled with an absorber might advantageously be employed to produce a series of spherical isodose surfaces, each surface with decreasing dose at greater and greater radii from the source.

Figure 2A:
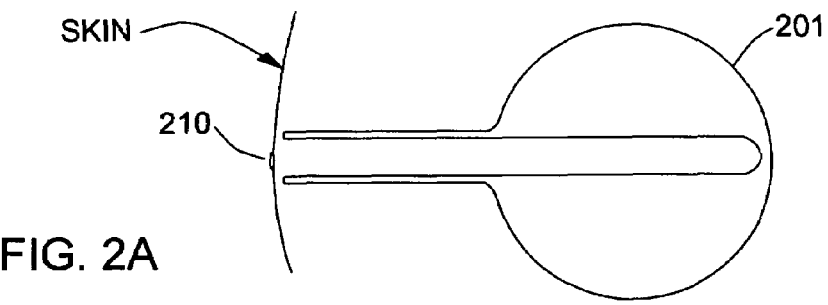
FIG. 2A is a schematic section view through tissue with an inflated balloon shown in an incision cavity, the balloon having an everted extension, the proximal end of the eversion lying near the skin.

FIGS. 2A and B depict a balloon 201 having a long radial extension 202, shaped somewhat like a test tube. The length of the extension is greater than the distance between the excision cavity and the skin. The balloon can be partially inflated and the extension everted, for example by a rod (not shown), and with the rod removed, placed within the cavity positioned for later access through a cut down procedure or percutaneous stick at a desired location through the skin. See FIG. 2A for this configuration. Palpation may be adequate to locate the extension, or if desired, the skin can be marked for future access, for example by a tattoo dot 210. Once positioned, the balloon can be fully inflated as described with respect to FIG. 1 above so as to maintain the cavity until radiation brachytherapy is commenced. The incision is then closed over the brachytherapy balloon apparatus to begin the healing process. No parts of the apparatus protrude through the skin once the incision is closed.

Figure 2B:
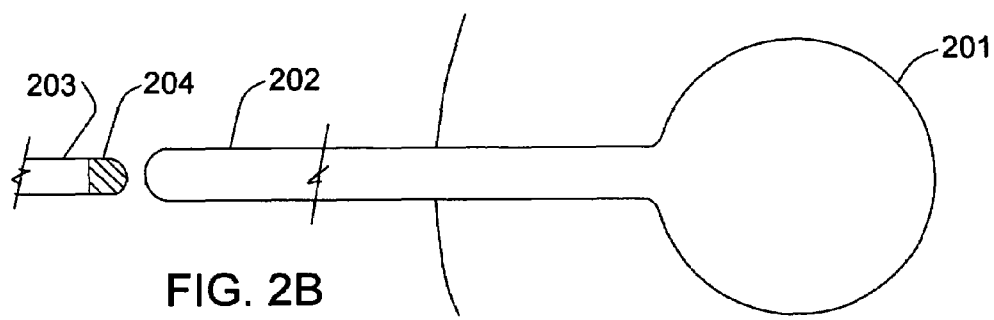
FIG. 2B is a schematic section view through tissue with access having been made through to the extension and the extension extended such that it extends fully outwardly from the skin.

When irradiation is to begin, the balloon extension 202 is accessed by percutaneous stick or incision, and the balloon extension withdrawn outwardly through the skin as shown in FIG. 2B. Note that balloon pressure will tend to make the extension evert spontaneously. The end of the extension can then be manipulated to allow insertion of a radiation source catheter 203. A preferred method is to insert a source catheter with a radiation source 204 at its tip into the extension such that the extension re-everts as the catheter is advanced into the balloon. Graduation marks 205 (FIG. 2C) on the catheter can be used to accurately position the depth of the catheter within the incision cavity. Such positioning can be confirmed by conventional imaging, and if desired, a clamp (not shown) can be used to secure the catheter within the protruding extension near its point of re-eversion to maintain the source position.

Figure 2C:
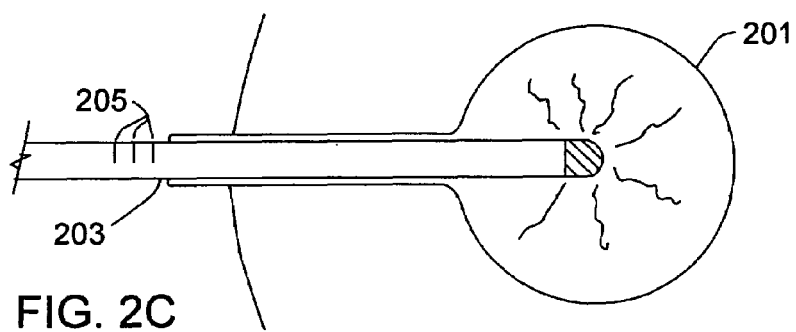
FIG. 2C is a schematic section view through tissue with the extension re-everted around a source catheter which has been inserted into the proximal tip of the extension and advanced into the balloon.

Rather than re-eversion as shown in FIG. 2C, the extension may be cut off and a conventional hub with internal seal (not shown; similar to that of FIG. 6C) attached in an appropriate manner to the extension. It may be necessary to reestablish balloon inflation after the catheter is started into the hub and balloon extension. Graduation marks may be used to indicate position of the catheter within the balloon. With the hub seal to maintain inflation pressure integrity, a separate channel (as shown in FIG. 2D, for example) can be provided alongside the balloon extension for inflation.

Figure 2D:
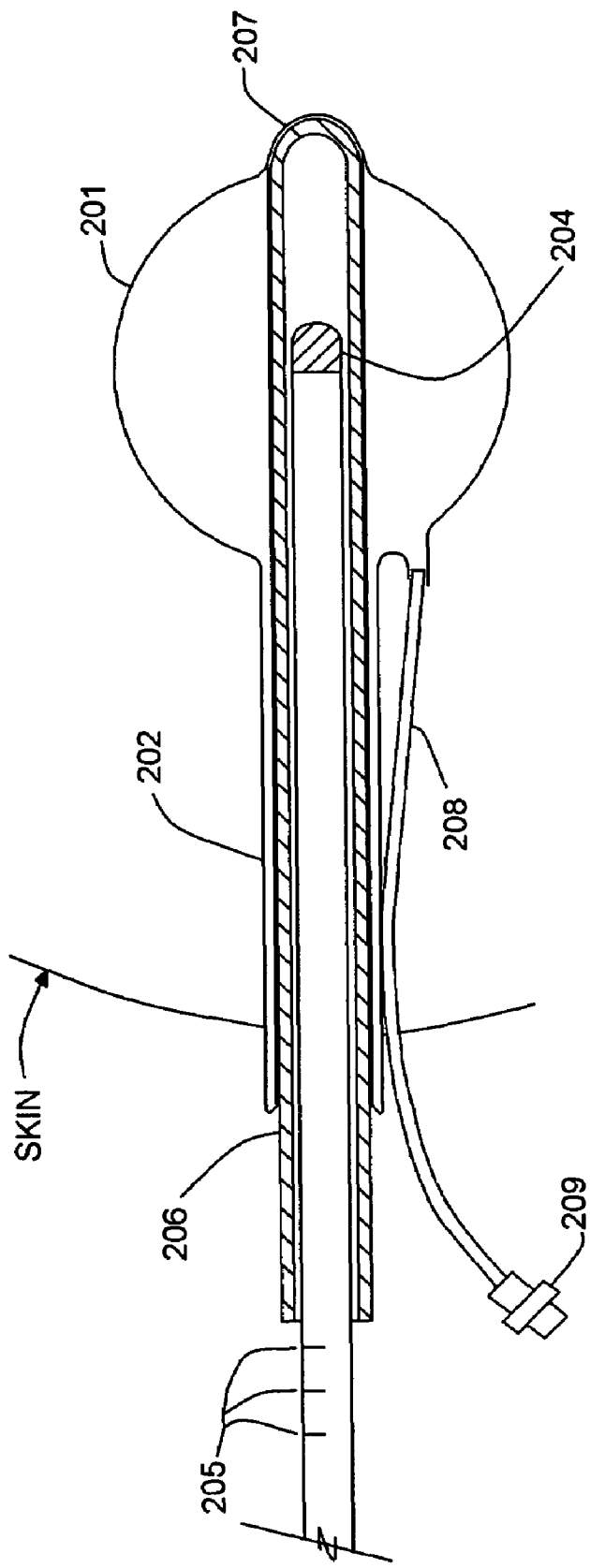
FIG. 2D is a similar section view through tissue with the extension re-everted around an inner sheath which has been inserted into the tip of the extension and advanced through the balloon and positioned within an optional centering pocket in the distal end of the balloon. A source catheter has been inserted into the inner sheath and advanced into the balloon. A balloon inflation tube with an in-line check valve has been provided alongside the balloon extension.

A particularly preferred embodiment is shown in FIG. 2D. As shown, it may be convenient to provide an inner sheath 206 which in conjunction with the hub, seal and an optional distal balloon centering pocket 207, facilitates accurate location of the source catheter. The inner sheath 206 serves to evert the extension 202 in the same manner as the catheter 203 in FIG. 2C. The optional distal centering pocket 207 cooperates with the distal tip of the inner sheath 206 and facilitates proper positioning of the source 204. Again, graduation marks 205 facilitate depth control of the catheter 203 relative to the proximal end of the inner sheath or the hub. Inflation of this embodiment is through a tube channel 208 adjacent to the balloon extension 202, and incorporates an in-line check valve 209 (Halkey-Roberts Corporation, St. Petersburg, Fla.).

Balloons of the nature described in FIGS. 1 and 2 can be fabricated by heat welding polymer sheet, for example polyurethane sheet (Deerfield Urethane, Inc., South Deerfield, Mass.) and subsequently pressure stretched at sufficient temperatures to form the desired shapes. Alternatively, they can be molded or formed from silicone rubber or other suitable polymers. Inflation channels such as that shown in FIG. 2D can be fabricated from tubing and components bonded together.

Figure 3A:
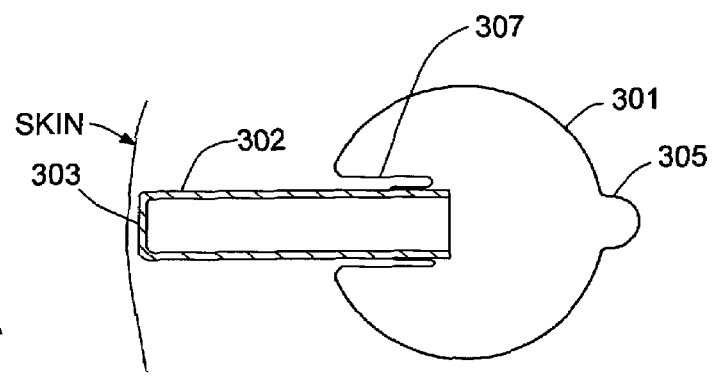
FIG. 3A is a schematic section view through tissue with an inflated balloon bonded to the distal end of an outer sheath, the proximal end of the sheath lying under but near the skin, and the proximal end of the balloon everted to accommodate the length of the sheath. The proximal end of the sheath is closed.
Figure 3B:
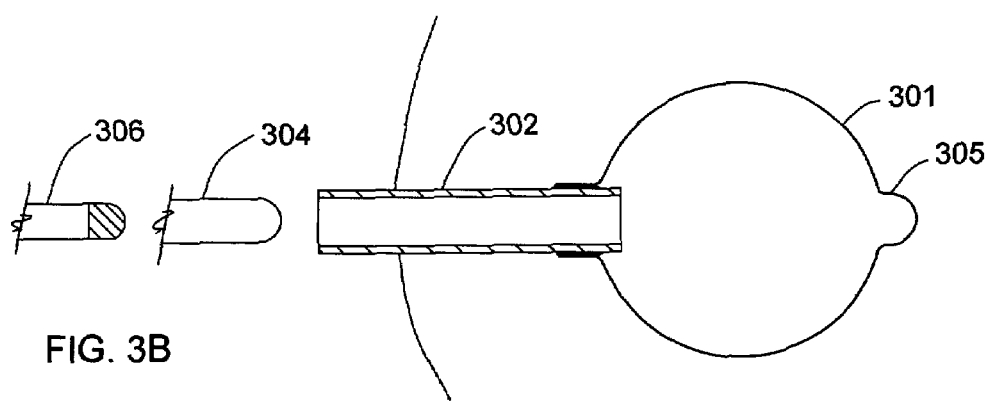
FIG. 3B shows the outer sheath of FIG. 3A having been accessed through the skin and extended outwardly from the skin, eliminating the balloon's eversion, with the end of the sheath removed.
Figure 3C:
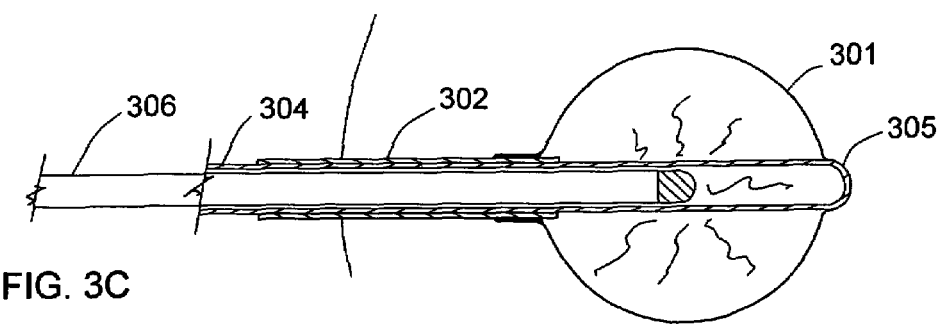
FIG. 3C shows the apparatus of FIG. 3B with an inner sheath inserted into the outer sheath and advanced fully into the balloon, thus engaging a central pocket at the distal end of the balloon and centering the inner sheath for source catheter positioning within the inner sheath.

FIGS. 3A, B and C depict a balloon 301 bonded to a tubular outer sheath 302 having a closed proximal end 303. The length of the sheath is such that when positioned under the skin in the desired location, the balloon must partially evert inwardly at 307 to accommodate the sheath length. Such a configuration is shown in FIG. 3A. When accessed to commence brachytherapy, the sheath 302 is withdrawn outwardly from the skin and the end 303 is cut off or otherwise removed, as shown in FIG. 3B. FIG. 3C shows the end of the sheath cut, and a conventional hub and seal (not shown, see FIG. 6C for a representative hub and seal) attached, for example by bonding, as described in connection with FIG. 2 above. An inner sheath 304 is then inserted into the outer sheath and advanced into the balloon. Optionally, a centering pocket 305 may be provided in the distal end of the balloon to locate the tip of the inner sheath. Proper positioning can be verified by conventional imaging. Such provision facilitates accurate location of the radiation catheter 306 which is positioned in the inner sheath 304 for brachytherapy. Because of provision of a seal in the hub between the inner and outer sheaths, the hub may conveniently incorporate an inflation port for the balloon since a sealed annular lumen is provided between sheaths. Alternatively, use of an inner sheath 304 may be eliminated, and catheter 306 may be inserted directly into the outer sheath 302 and advanced into the balloon 301 for brachytherapy treatment.

Figure 4B:
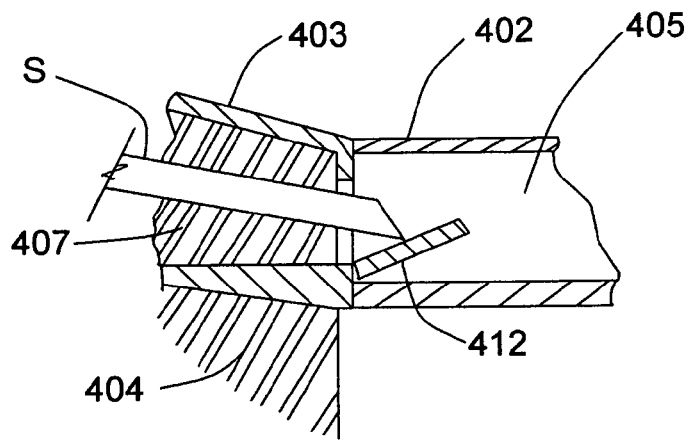
FIG. 4B is a detail of a part of FIG. 4A schematically depicting a trap-door type one-way valve in the inflation channel of the apparatus.
Figure 4A:
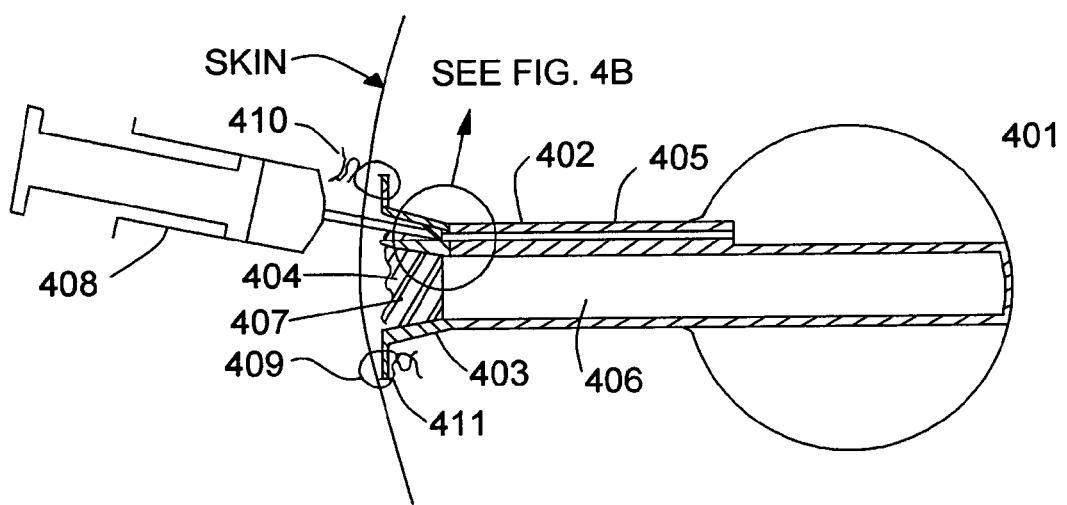
FIG. 4A is a schematic section view through tissue showing a balloon and sheath implanted, and further comprising a housing secured under the skin and in communication with the sheath and balloon. A syringe is shown injecting inflation medium into the balloon.

FIG. 4A shows a balloon 401 and sheath 402 with a receptacle or housing 403 at the proximal end of the sheath 402. The sheath preferably is secured (for example by bonding) at both the proximal and distal ends of the balloon 401, and to the distal side of the housing 403. The sheath length is substantially fixed compared to the apparatus previously described with respect to that of FIGS. 2 and 3. The housing 403 is divided into two sections, a larger section 404 for the radiation source catheter (not shown), and a smaller for syringe access to a balloon inflation channel 405 positioned alongside the source catheter channel 406. The housing may further comprise features which provide tactile feedback from outside of the patient's skin to assist locating and identifying individual channels, facilitating percutaneous access. Such features would include sized, positioned or shaped openings, or protrusions which can be felt by hand.

Both housing sections are filled with self sealing gel or silicone rubber 407 as described previously, and both are tapered or beveled such that a syringe 408 in the case of inflation, or a sheath extension for purposes of creating convenient source catheter access, can be guided into proper engagement with their respective channels percutaneously, or with the help of a cut-down procedure. Ring-like or other appendages or flanges with holes 411 are molded onto the exterior of the housing to facilitate suturing the housing to the skin. An inflation syringe 408 is shown inflating the balloon. Sutures are shown fastening the housing 403 to the patient's skin, an exemplary suture 410 from without the patient, and another suture 409 from within. Either approach may be used, and suturing may be through the entirety of the skin, or may be (from the inside) only through the subcutaneous layer.

FIG. 4B shows a detail of the inflation channel 405 distal of the housing 403. If the self sealing material is not strong enough to maintain inflation of the balloon, a valve 412 may be provided to maintain inflation. The valve illustrated in FIG. 4B is a conventional flapper type check valve on a molded live hinge, with syringe needle S shown holding it in an open position.

Figure 4C:
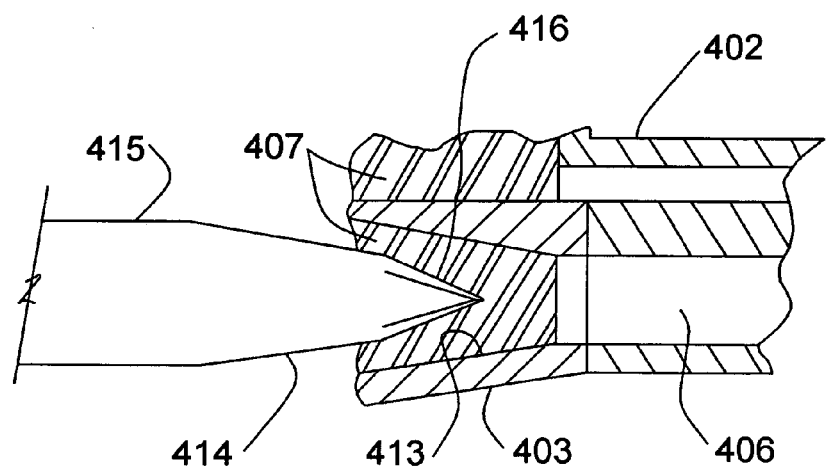
FIG. 4C is a section view showing self-sealing gel filler within the housing, with the central source channel being accessed by a hollow, split, percutaneous trocar-style sheath extension.
Figure 4D:
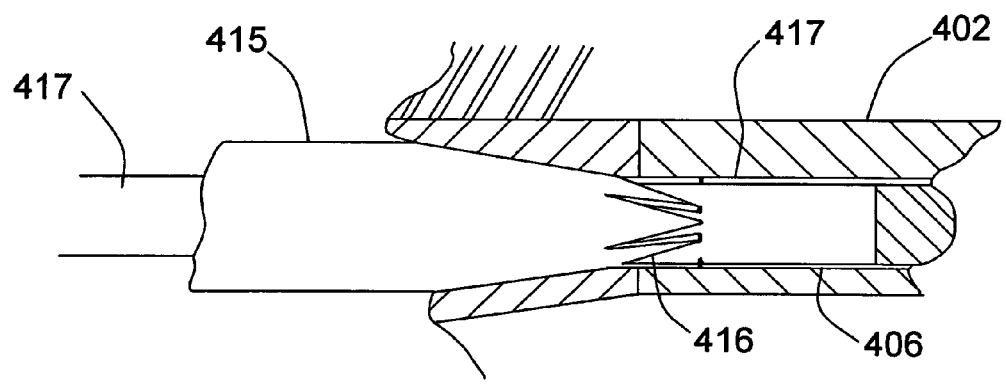
FIG. 4D shows the apparatus of FIG. 4C with a source catheter inserted through the now fully seated split trocar sheath extension.

FIG. 4C shows a detail of the housing 403 in section, with a female tapered bore 413 to accept a male taper 414 of a split-tip trocar style sheath extension 415. The sheath extension 415 is shown entering the bore, to seat in the source catheter channel 406 behind the receptacle or housing 403. FIG. 4D shows the trocar extension seated (if necessary, with removal of self-sealing material 407 to facilitate the seating) and the tip 416 spread open by the source catheter 417 advancing toward the balloon (not shown) through the source catheter channel 406 in the outer sheath 402.

Figure 5A:
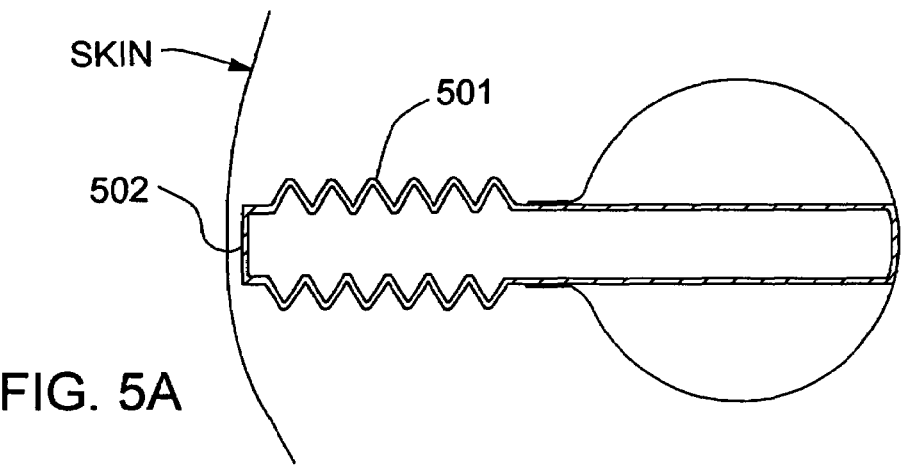
FIG. 5A is a section view through tissue, schematically showing an alternate sheath embodiment having a convoluted or pleated shaft. The proximal end of the sheath is closed.
Figure 5B:
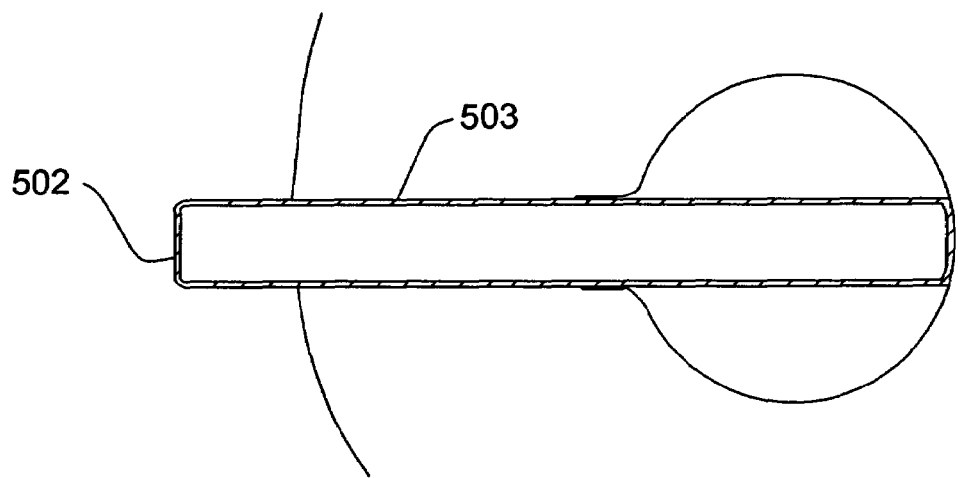
FIG. 5B is a view of the embodiment of FIG. 5A with the proximal end of the convoluted sheath having been accessed through the skin and extended outwardly from the skin of the patient.

FIG. 5A depicts an alternate sheath design with a convoluted or pleated extendable shaft 501. With this design, the proximal end 502 of the sheath 501 may be grasped, extended and withdrawn free of the skin as shown in FIG. 5B, and treated similarly to the sheath 302 of FIG. 3, including cutting off the end 502. As an alternate to convolutions, the sheath can be elastomeric, and stretched to mimic the sheath of, for example, FIGS. 2A-2D.

Figure 6A:
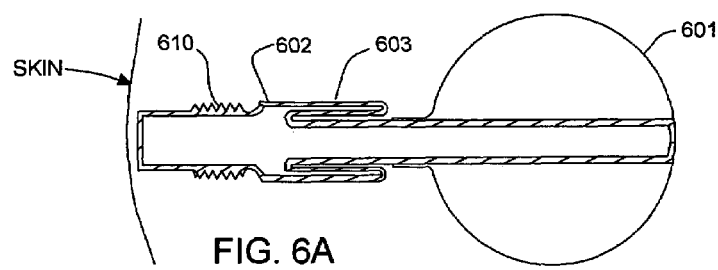
FIG. 6A is a section view through tissue showing an inflated balloon with another embodiment of a sheath having an everted shaft positioned under the skin.
Figure 6B:
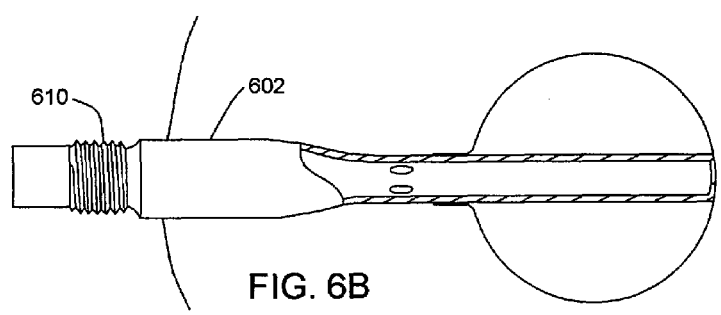
FIG. 6B is a view of the apparatus of FIG. 6A with the sheath having been accessed and extended, with the eversion thus eliminated and the closed end removed.
Figure 6C:
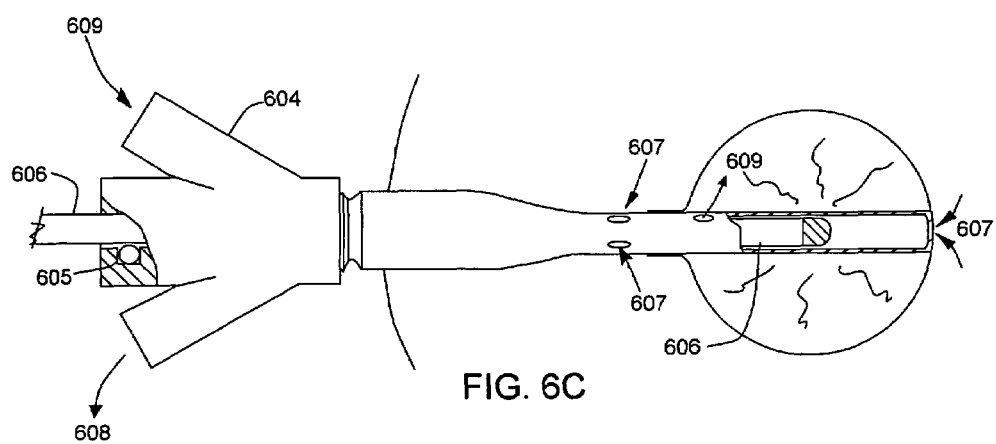
FIG. 6C is a view of the apparatus of FIG. 6B with a conventional hub attached to the proximal end of the sheath, and a source catheter inserted into the sheath and advanced into the balloon. A conventional seal has been provided within the hub to allow a suction channel to drain the excision cavity.

FIG. 6A shows a balloon 601 and sheath 602 with an everted section 603 outside the balloon, such that the sheath section 603 folds over itself in coaxial configuration. The sheath 602 extends through the length of the balloon 601 and in this embodiment is fastened at its distal end (as by bonding for example) to the distal end of the balloon 601. After a cutdown, this sheath can be withdrawn and everted such that the proximal end of the sheath extends free of the skin as shown in FIG. 6B. This embodiment too can be fitted with a hub 604, for example by threads 610, and with an internal seal 605 for the source catheter 606, as shown in FIG. 6C. Alternately to cutting the end of sheath 602 to affix hub 604, a threaded cap (not shown) can be provided which can be removed in order to fix the hub 604 to the sheath 602. In this case, the annulus between the sheath 602 and the catheter 606 is utilized for suction from within the incision cavity for seroma and the like, as indicated by the arrows 607 at the distal end of the balloon 601, and adjacent to the proximal end of the balloon. Suction applied at the arrow 608 will serve to evacuate the excision cavity. Features on the surface of the balloon 601 in accordance with the teachings of Ser. No. 11/639,495, as well as Ser. No. 10/683,885, both referenced above, can be used to provide distributed suction capability over the surface of the balloon 601. Alternately, if the suction channel is reversed, again according to the teachings of Ser. No. 11/639,495, the channel can be used to infuse therapeutic or anesthetic agents into the cavity outside of the balloon 601, or outside the shaft 602. Anaesthetic can be administered to ease discomfort of the patient on removal of the applicator or on inflation of the balloon or re-inflation. If an inflation channel is desired, a second auxiliary port can be provided on the hub 604 communicating with a small lumen within the wall of the sheath (not shown) in a conventional manner. Arrows 609 indicate this channel.

Figure 7A:
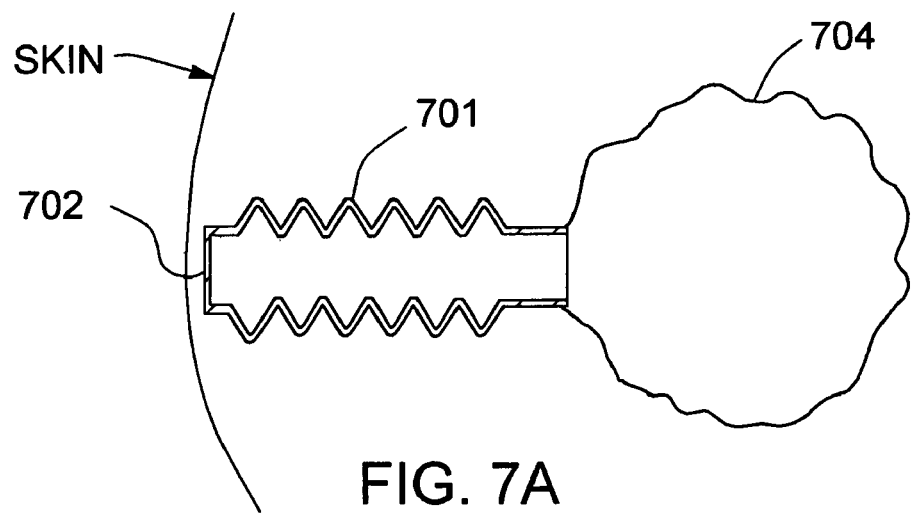
FIGS. 7A and B are section views through body tissue which show an implanted sheath similar to that of FIG. 5A, without a balloon, the sheath being later accessed and drawn outward (FIG. 7B) in a way similar to that shown in FIG. 5B.
Figure 7B:
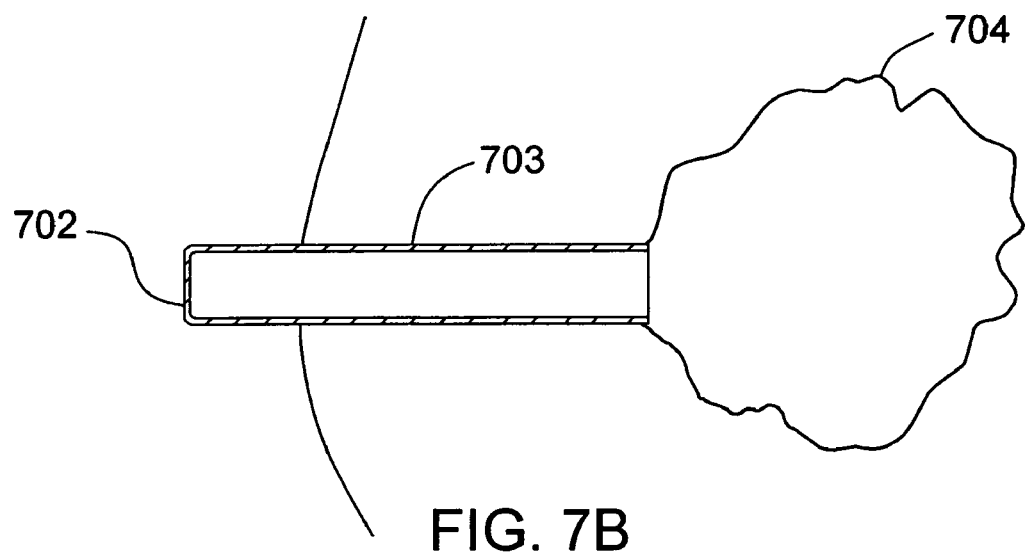

FIG. 7A shows schematically an implanted, convoluted sheath 701 without balloon positioned between incision cavity 704 and the skin of the patient. The sheath 701 has a closed proximal end 702. FIG. 7B shows the sheath 701 of FIG. 7A having been reaccessed by cut down through the skin or other means, and drawn outward. Once proud of the skin, the closed end 702 is then removed, providing open access to the incision cavity for inserting of further brachytherapy apparatus into the cavity, preferably a conventional applicator and miniature x-ray source (now shown), and subsequent radiotherapy. A hub (not shown) may be used as in preceding embodiments if desired.

Figure 8A:
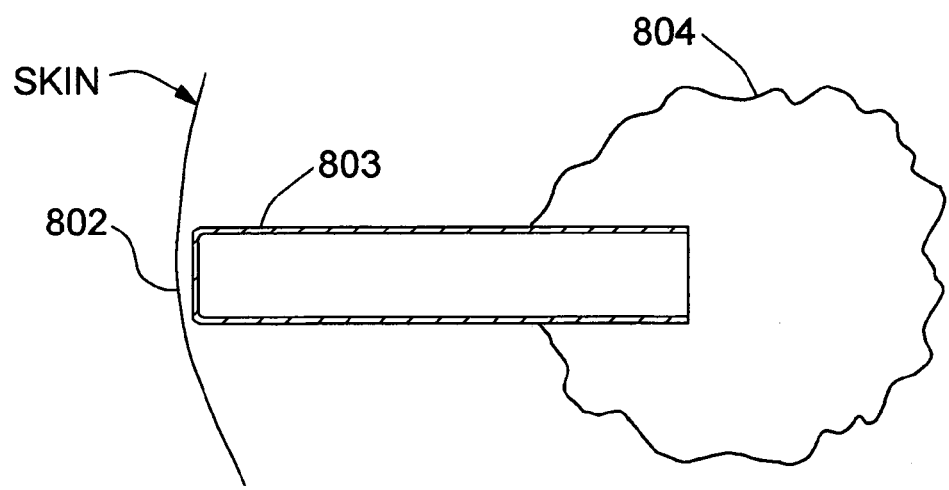
FIG. 8A is a section view through body tissue showing a straight sheath implanted under the skin of the patient with its distal end well into the incision cavity following surgery.
Figure 8B:
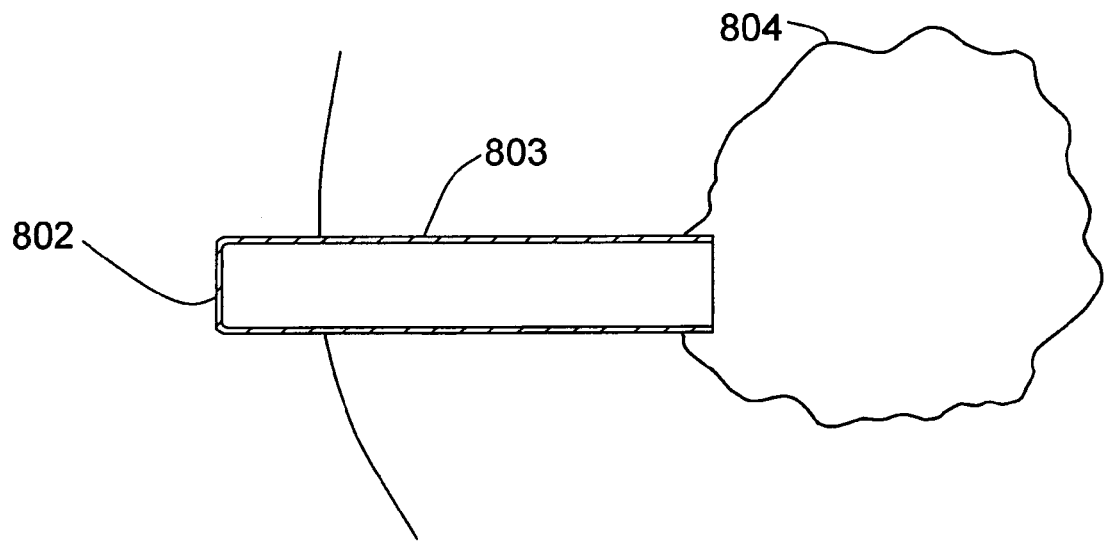
FIG. 8B is a section view of the sheath of FIG. 8A having been reaccessed through the skin of the patient and drawn outwards in much the same manner as the sheath of FIG. 7B.

FIGS. 8A and 8B schematically show a similar sheath 803 apparatus to that of FIG. 7A, but rather than having a convoluted shaft, the sheath is straight and extends well into the cavity 804 when contained under the skin. After positioning the sheath 803, the incision is closed in the manner described above, and the incision cavity allowed to collapse around the implanted sheath during the healing process. FIG. 8B shows the sheath 803 having been reaccessed and partially withdrawn above the skin such that the closed end 802 can be removed, all without losing access to the incision cavity 804. Subsequently, radiotherapy commences in the manner described above in connection with FIGS. 7A and 7B.

Figure 9:
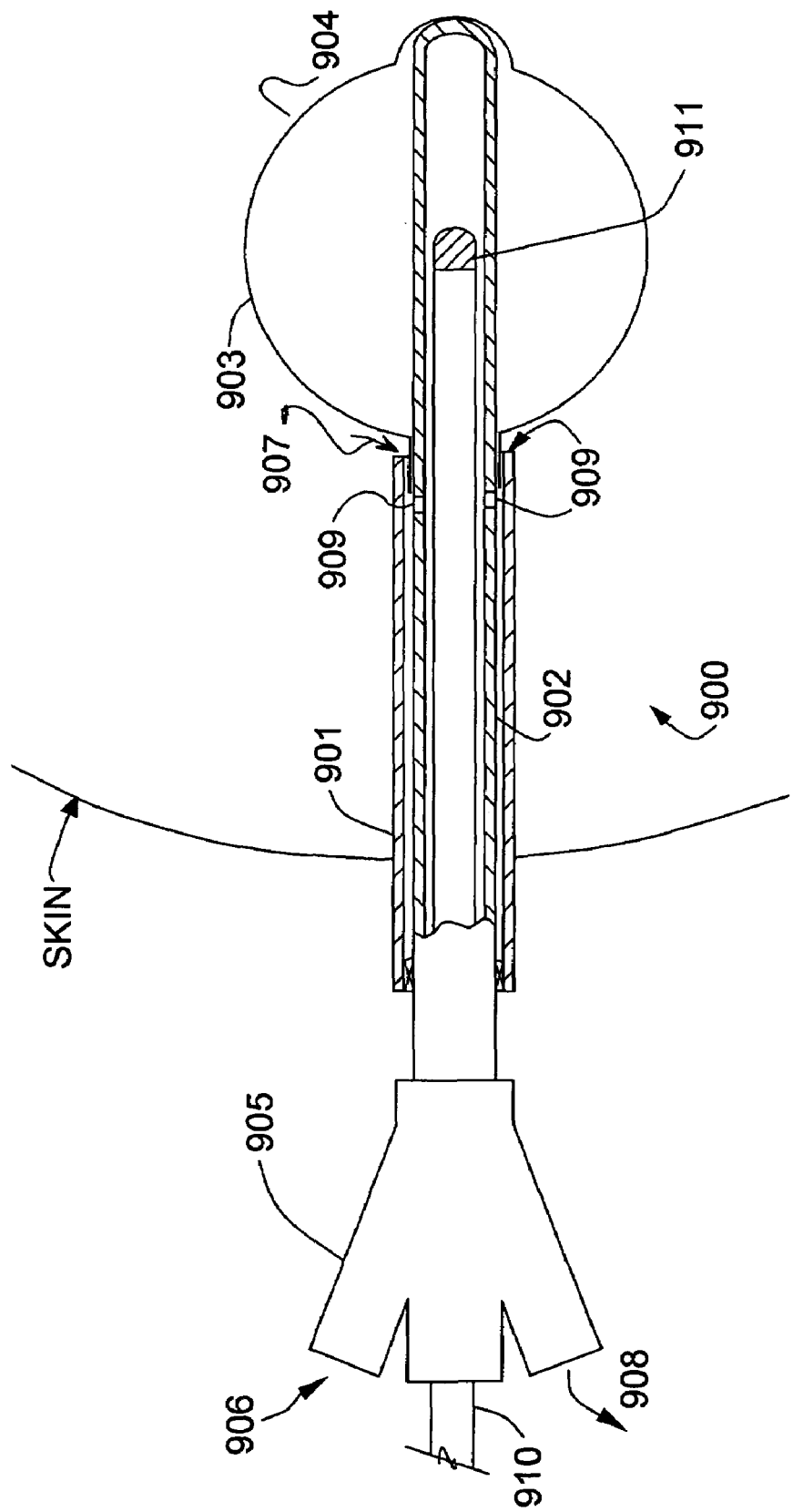
FIG. 9 is a section view through tissue showing an implanted sheath of FIG. 7 or 8, with its closed end removed and with an inner sheath comprising a balloon and hub inserted into the implanted sheath. A source catheter is shown within the inner sheath for purposes of irradiating the inside of the incision cavity.

FIG. 9 depicts schematically an apparatus 900 comprising an implanted sheath structure 901 of FIG. 7 or 8, but in addition, an inner sheath 902 having a balloon 903 proximal of its distal end has been inserted into an incision cavity 904. At the proximal end of the inner sheath 902, a hub 905 is affixed, for example by bonding, and provides balloon inflation through a port 906 at the upper hub arm, and through a conventional port and lumen (neither shown) within the wall of the inner sheath 902. The hub 905 also provides suction (see flow arrow 907) through the annulus between the sheaths 901 and 902 though a port 908 at the lower arm of the hub 905 and sheath ports 909 near the proximal end of the balloon 903 in the inner sheath 902. A seal 912 at the proximal end of the sheath 901 provides pressure integrity for the suction channel. Reversing this fluid circuit will provide for infusion of therapeutic agents or anesthetic.

Within the inner sheath 902 and the hub 905 a source catheter 910 is inserted having a source 911 at its distal tip.

Several collateral features may be incorporated variously into the embodiments described above. The following are examples:

Radiation attenuating patches or balloon segments, or spacers, placed on or adjacent to balloons of the implanted apparatus, can be used locally to moderate radiation intensity, thus tailoring radiation output to variations in anatomy or prescription. Such radiation moderating devices are discussed in co-pending application Ser. No. 11/385,255, filed Mar. 20, 2006, the specification of which is incorporated herein in its entirety.

Embodiments with provision for drainage and agent infusion are described above. Exemplary apparatus and methods are described in co-pending application Ser. Nos. 11/639,495, filed Dec. 16, 2005, and 10/683,885, filed Oct. 10, 2003, the specifications of which are incorporated herein in its entirety.

The basic devices and methods of use described above, with or without the collateral features or techniques described, may be used in various combinations and permutations without departing from the scope of this invention. Each embodiment described preferably includes a portion of the applicator apparatus which, when reaccessed for radiotherapy, establishes an extension outside the skin that facilitates creation of an infection barrier for the duration of the prescribed therapy. The utility of these combinations will be apparent to those skilled in the art, as will variations to these embodiments

We claim:

1. A method for brachytherapy radiation treatment of tissue beneath the skin of a patient, including for accessing and re-accessing a target site beneath the skin, comprising:
   identifying a cavity within a patient, beneath the skin of the patient,
   defining a path through the skin to the cavity, including making an incision if the skin is closed along the path,
   inserting an applicator through the skin along said path,
   the applicator having a sheath for extending from the skin to the cavity, and the sheath having two modes, a receded mode in which the sheath is stored under the skin and an extended mode in which the sheath extends through the skin to the exterior of the patient while still reaching the cavity,
   the applicator including a lumen in the sheath adapted to receive a catheter or shaft carrying at its distal end a source of radiation,
   following implantation of the applicator under the skin, either after a first brachytherapy radiation application using the applicator or prior to any such brachytherapy application, closing the skin over the receded applicator sheath,
   at a later time, after the skin has been closed, re-accessing the sheath of the applicator by (a) opening the skin, (b) accessing a proximal end of the sheath and causing the sheath to extend out through the skin to the extended mode so that the proximal end of the sheath protrudes out from the skin, (c) opening the proximal end of the sheath, (d) inserting a catheter or shaft with a radiation source into the sheath so that the source enters the cavity, (e) irradiating target tissue from the applicator within the cavity, and (f) returning the sheath to the receded mode and re-closing the skin, if further, later treatments are needed, and
   repeating steps (a) through (f) for further treatments as needed and in accordance with a radiation prescription, except in a final treatment repeating steps (a) through (e) and subsequently removing the applicator after all treatments have been completed.

2. The method of claim 1, wherein the sheath comprises an everting sheath which everts inwardly with its proximal end turned coaxially inward in the receded mode.

3. The method of claim 2, wherein the applicator includes an inflatable balloon, with the everting sheath extending from and communicating with a proximal end of the balloon.

4. The method of claim 1, wherein the proximal end of the sheath includes a screw thread, and further including a hub with multiple ports, adapted to screw onto the screw threads of the sheath.

5. The method of claim 4, wherein the sheath includes a collapsing feature for shortening its length in the receded mode.

6. The method of claim 5, wherein the sheath's collapsing feature comprises an everting section whereby the sheath folds coaxially over itself in the everting section in the receded mode.

7. The method of claim 5, wherein the sheath's collapsing feature comprises a convoluted or pleated section allowing retraction to the receded mode.

8. The method of claim 1, wherein the sheath has a convoluted or pleated section allowing retraction to the receded mode.

9. The method of claim 1, wherein the sheath has an everting section whereby the sheath folds coaxially over itself in the everting section in the receded mode.

10. The method of claim 1, wherein the applicator includes an inflatable balloon, with a proximal opening in the balloon through which the sheath is slidable into the balloon to form the receded mode.

11. The method of claim 1, wherein the sheath is positioned to slide deeply inward of the cavity to form the receded mode.

12. The method of claim 1, including, in step (d), inserting an inner sheath into and through the extended sheath, the inner sheath having secured to it an inflatable balloon, and including the step of inserting the inner sheath with balloon deflated through the extended sheath until the balloon resides in the cavity, then inflating the balloon, and inserting a source catheter carrying a radiation source into the balloon in the cavity via the inner sheath.

13. The method of claim 1, wherein the cavity is within a breast.

14. The method of claim 1, wherein the applicator has one or more ports open to the patient's tissue, and further including the step of infusing an anesthetic agent through the ports of the applicator into the patient's tissue adjacent to the cavity to reduce discomfort of the patient during applicator insertion, removal or manipulation.

15. The method of claim 1, wherein the applicator includes an inflatable balloon, and including a step of infusing an anesthetic agent through the applicator into the patient's tissue adjacent to the cavity to decrease patient discomfort during applicator insertion, balloon inflation, or removal of the applicator.

16. A method for brachytherapy radiation treatment of tissue beneath the skin of a patient, including for accessing and re-accessing a target site beneath the skin, comprising:
   identifying a cavity within a patient, beneath the skin of the patient,
   defining a path through the skin to the cavity, including making an incision if the skin is closed alona the path,
   inserting an applicator through the skin along said path,
   the applicator having a sheath with a proximal end positioned to lie just beneath the skin, and the proximal end of the sheath comprising a housing with a penetrable sealant closing a lumen of the sheath, the lumen of the sheath being configured to receive a catheter or shaft carrying a source of radiation,
   following implantation of the applicator under the skin, either after a first brachytherapy radiation application using the applicator or prior to any such brachytherapy application, closing the skin over the applicator sheath, at a later time, after the skin has been closed, inserting a split-tip trocar style sheath extension through the skin and into the sealant in the housing, then pushing a catheter carrying a radiation source through the sheath extension and through the sheath and into the cavity, wherein the applicator includes a balloon and wherein the housing at the proximal end of the sheath includes an inflation channel separate from and alongside said lumen, the channel having a proximal end with self-sealing material in the channel, the channel being sized to receive a syringe inserted through the skin for the purpose of inflating the balloon, and the method including using a syringe to pierce the skin, access the balloon inflation channel and inflate the balloon prior to irradiation of the target tissue, irradiating target tissue in accordance with a prescription using the radiation source within the cavity and within the balloon, removing the catheter, source and sheath extension from the applicator, and closing the skin, and repeating the steps of penetrating the skin and inserting a sheath extension into and through the sealant, inserting the catheter and irradiating, as required in accordance with the radiation prescription.

* * * * *